United States Patent
Roussel

(10) Patent No.: US 7,041,302 B2
(45) Date of Patent: May 9, 2006

(54) THERAPEUTIC MODULATION OF THE TUMOR INFLAMMATORY RESPONSE

(75) Inventor: Eugene Roussel, Houston, TX (US)

(73) Assignee: BioTHER Corporation, Houston, TX (US)

( * ) Notice: Subject to any disclaimer, the term of this patent is extended or adjusted under 35 U.S.C. 154(b) by 0 days.

(21) Appl. No.: 09/756,978

(22) Filed: Jan. 9, 2001

(65) Prior Publication Data

US 2002/0090353 A1 Jul. 11, 2002

(51) Int. Cl.
*A61K 39/00* (2006.01)
*A61K 38/20* (2006.01)
*A61K 38/21* (2006.01)
*A61K 35/12* (2006.01)
*A61K 35/14* (2006.01)

(52) U.S. Cl. .................. 424/278.1; 424/85.1; 424/85.2; 424/85.4; 424/93.21; 424/94.63; 424/94.64; 424/94.65; 424/94.66; 424/277.1; 424/530; 424/534

(58) Field of Classification Search ................ 424/85.1, 424/85.2, 85.4, 93.21, 93.7, 94.63, 94.64, 424/94.65, 94.66, 277.1, 278.1, 530, 534, 424/94.2, 184.1, 94.1; 514/2

See application file for complete search history.

(56) References Cited

U.S. PATENT DOCUMENTS

| 4,879,111 | A |   | 11/1989 | Chong |
|---|---|---|---|---|
| 5,082,658 | A |   | 1/1992 | Palladino |
| 5,446,033 | A |   | 8/1995 | Engel et al. |
| 5,474,981 | A |   | 12/1995 | Luster et al. |
| 5,871,723 | A |   | 2/1999 | Strieter et al. |
| 6,011,047 | A | * | 1/2000 | Semple et al. ............... 514/327 |
| 2002/0044919 | A1 | * | 4/2002 | Yu ............................. 424/85.1 |
| 2002/0090381 | A1 | * | 7/2002 | Bottomly et al. ......... 424/198.1 |

FOREIGN PATENT DOCUMENTS

| EP |   | 310136 | * | 2/1997 |
|---|---|---|---|---|
| WO | WO | 92/01039 | * | 1/1992 |
| WO | WO | 98/36768 | * | 8/1998 |
| WO |   | 99/59599 |   | 11/1999 |
| WO |   | 00/01392 |   | 1/2000 |
| WO |   | 01/62274 |   | 8/2001 |

OTHER PUBLICATIONS

Mori, et al., 1993, Int J Gynecol Cancer 3(1):36–43.*
Zeisig, et al., 1994, Anticancer Res, 14(5A):1785–9.*
Wuyts, et al., 1994, J Immunol Methods, 174(1–2):237–47.*
Akatov, et al., 2000, Biosci Rep, 20(5):411–7.*
Schrauzer, 2000, Cell Mol Life Sci, 57(13–14):1864–73.*
Demer, et al., BIOTECHNOLOGY, vol. 12, p. 320, Mar. 1994.*
Jain et al., Cancer and Metatasis Review, vol. 9, pp. 253–266.*
Berke and Rosen, Transplantation Proceedings, 1987, vol. XIX, pp. 412–416).*
abstract of Curtiss (Arteriosclerosis and Thrombosis, 1994, vol. 14, pp. 47–53).*
U.S. Appl. No. 60/177,024, filed Jan. 19, 2000.*
Nishimura et al (Cancer Chemother Pharmacol, 2000, vol. 46 (suppl.), pp. S52–S61).*
Cameron et al (Journal of Experimental Medicine, 1990, vol. 171, pp. 249–263).*
Ferrero et al (European Journal of Immunology, 1998, vol. 28, pp. 2530–2536).*
Rovere et al (Journal of Immunology, 1998, vol. 161, pp. 4467–4471).*
Mollinedo et al (Cancer Research, 1997, vol. 57, pp. 1320–1328).*
Boggs et al (Biochimica et Biophysica Acta, 1998, vol. 1389, pp. 1–12).*
Garcia–Zepeda et al (Nature Medicine, 1996, vol. 2, pp. 449–456).*
Wang et al (Molecular and Cellular Biology, 1995, vol. 15, pp. 1759–1768).*
Ausubel et al (Short Protocols in Molecular Biology, second edition, 1992 p. 1–20).*
abstract of DeSanctis et al (Seminars in Interventional Radiology, 1997, vol. 14, pp. 255–284).*
abstract of Aker (Cancer, 1979, vol. 43, suppl., pp. 2103–2107).*
abstract of Johnston (Journal of Human Nutrition, 1979, vol. 33, pp. 189–196).*
Tuting et al (Journal of Immunology, 1998, vol. 160, pp. 1139–1147).*
Lee et al (J Immunol. Jan. 1, 2000: 164: 231–9).*
Tannenbaum et al (J Immunol. 1998: 161: 927–932).*
Lanni et al (Proc Natl Acad Sci USA vol. 94, pp. 9679–9683).*
Chou et al (1997, Bioelectromagnetics, vol. 18, p. 14–24, abstract only).*
Habal (1980, J Biomer Mater Res, vol. 14, pp. 789–801, abstract only).*
Wemyss–Holden et al (2000, J Surg Res, vol. 93, pp. 55–62).*
Tamai et al (2000, Oncol Rep, vol. 719, pp. 719–723), Abstract only Apr. 6, 2003.*
Gallucci et al, 2001, Curr Opin Immunol, vol. 13, pp. 114–119.*

(Continued)

Primary Examiner—Karen A. Canella
(74) Attorney, Agent, or Firm—Oblon, Spivak, McClelland, Maier & Neustadt, P.C.

(57) ABSTRACT

The invention relates to compositions, kits, and methods for alleviating cancer (i.e., a tumor) in a human patient. The therapeutic modality effected by the invention involves inducing a type 1 inflammatory response in the tumor tissue, whereby the tumor tissue is diminished or destroyed and the patient develops immune memory that inhibits or prevents recurrence of the tumor.

64 Claims, No Drawings

OTHER PUBLICATIONS

Yamamoto et al (2003, Int J Cancer, vol. 103, p. 822 abstract only).*

Dabrowska et al (2000, Anticancer Res, vol. 20, pp. 391–394 abstract only).*

Kondoh et al (2003, Breast Cancer Res Treat, vol. 78, pp. 37–44).*

Jaroszeski et al (1997, Biochim Biophys Acta, vol. 1334, pp. 15–18).*

Svedersky L.P., et al. "Enhanced Antitumor Activity of Recombinant Interferon Gamma in Combination with Tumor Necrosis Factors and Chemotherapeutic Agents" International Journal of Immunopharmacology, vol. 7, No. 3, 1985, p. 330.

Lumsden, et al., "Improved efficacy of doxorubicin by simultaneous treatment with interferon and interleukin–2," in vivo 6:553–8 (1992).

Akbar et al., "IFN–α and IFN–β: a link between immune memory and chronic inflammation," Immunol. Today 21(7):337–342 (2000).

Asselin–Paturel et al., "Quantitative analysis of Th1, Th2 and TGF–beta1 cytokine expression in tumor, TIL and RBL of non–small cell lung cancer patients," Int. J. Cancer 77(1):7–12 (1998) (Abstract only).

Azavedo et al., "Radiological evidence of response to electrochemical treatment of breast cancer," Clin. Radiol. 43:84–87 (1991).

Baggiolini et al., "Human Chemokines: an update," Annu. Rev. Immunol. 15:675–705 (1997).

Bellone et al., "Tumor–associated transforming growth factor–beta and interleukin–10 contribute to a systemic Th2 immune phenotype in pancreatic carcinoma patients," Am. J. Pathol. 155(2):537–547 (1999) (Abstract only).

Bendich, "New data on vitamin C intake," Nutrition 13(2):154–155 (1997).

Bonagura et al., "Recurrent respiratory papillomatosis: altered CD8(+)T–cell subsets and T(H)1/T(H)2 cytokine imbalance," Clin. Immunol. 93(3):302–311 (1999) (Abstract only).

Camp et al., "In situ cytokine production by breast cancer tumor–infiltrating lymphocytes," Ann. Surg. Oncol. 3(2):176–184 (1996) (Abstract only).

Clive et al., "Miltefosine as a topical treatment for cutaneous metastases in breast carcinoma," Cancer Chemother. Pharmacol. 44 (Suppl):S29–S30 (1999).

Colantonio et al., "Upregulation of integrin α6/β1 and chemokine receptor CCR1 by Interleukin–12 promotes the migration of human type 1 helper T cells," Blood 94(9):2981–2989 (1999).

Constant et al., "Induction of Th1 and Th2 CD4+T cell responses: The alternative approaches," Annu. Rev. Immunol. 15:297–322 (1997).

Del Prete, "Human Th1 and Th2 lymphocytes: their role in the pathophysiology of atopy," Allergy 47(5):450–455 (1992) (Abstract only).

Del Prete, "The concept of type–1 and type–2 helper T cells and their cytokines in humans" Int. Rev. Immunol. 16(3–4):427–455 (1998) (Abstract only).

Echchakir et al., "Analysis of T–cell–receptor β–chain–gene usage in peripheral–blood and tumor–infiltrating lymphocytes from human non–small–cell lung carcinomas," Int. J. Cancer 81:205–213 (1999).

Elsasser–Beile et al., "Th1 and Th2 cytokine response patterns in leukocyte cultures of patients with urinary bladder, renal cell and prostate carcinomas," Tumour Biol. 19(6):470–476 (1998) (Abstract only).

Fleischmann et al., "Systemic effects of orally administered interferons and interleukin–2," J. Interferon Cytokine Res. 19:829–839 (1999).

Fujimoto et al., "Streptococcal preparation OK–432 is a potent inducer of IL–12 and a T helper cell 1 dominant state," J. Immunol. 158(12):5619–5626 (1997) (Abstract only).

Fujisao et al., "Th1/Th2 balance alteration in the clinical course of a patient with pure red cell aplasia and thymoma," Br. J. Haematol. 103(2):308–310 (1998) (Abstract only).

Gallucci et al., "Danger signals: SOS to the immune system," Curr. Op. Immunol. 13:114–119 (2001).

Ghosh et al., "Gradual loss of T–helper 1 populations in spleen of mice during progressive tumor growth," J. Natl. Cancer Inst. 87(19):1478–1483 (1995) (Abstract only).

Gingras et al., "Comparison of cell adhesion molecule expression between glioblastoma multiforme and autologous normal brain tissue," J. Neuroimmunol. 57(1–2):143–153 (1995) (Abstract only).

Gingras et al., "Little expression of Cytokine mRNA by fresh tumor–infiltrating mononuclear leukocytes from glioma and lung adenocarcinoma," Cytokine 7(6):580–588 (1995).

Goedegebuure et al., "Simultaneous production of T helper–1–like cytokines and cytolytic activity by tumor–specific T cells in ovarian and breast cancer," Cellular Immunol. 175:150–156 (1997).

Gorelik et al., "Low–dose melphalan–induced shift in the production of a Th2–type cytokine to a Th1–type cytokine in mice bearing a large MOPC–315 tumor," Cancer Immunol. Immunother. 39:117–126 (1994).

Gorelik et al., "Low–dose–melphalan–induced up–regulation of type–1 cytokine expression in the s.c. tumor nodule of MOPC–315 tumor bearers and the role of interferon gamma in the therapuetic outcome," Cancer Immunol. Immunother. 41(6):363–374 (1995) (Abstract only).

Goto et al., "Analysis of Th1 and Th2 cytokine production by peripheral blood mononuclear cells as a parameter of immunological dysfunction in advanced cancer patients," Cancer Immunol. Immunother. 48(8):435–442 (1999) (Abstract only).

Inagawa et al., "Mechanisms by which chemotherapeutic agents augment the antitumor effects of tumor necroses factor: involvement of the pattern shift of cytokines from Th2 to Th1 in tumor lesions," Anticancer Res. 18(5D):3957–3964 (1998) (Abstract only).

Ito et al., "Lung carcinoma: analysis of T helper type 1 and 2 cells and T cytotoxic type 1 and 2 cells by intracellular cytokine detection with flow cytometry," Cancer Immunol. Immunother. 48(4):204–208 (1999) (Abstract only).

Jackson et al., "Prognosis of intravesical bacillus Calmette–Guerin therapy for superficial bladder cancer by immunological urinary measurements: statistically weighted syndrome analysis," J. Urol. 159(3):1054–1063 (1998) (Abstract only).

Khar et al., "High intratumoural level of cytokines mediates efficient regression of a rat histiocytoma," Clin. Exp. Immunol. 110(1):127–131 (1977).

Kurt et al.., "T lymphocytes infiltrating sites of tumor rejection and progression display identical Vβ usage but different cytotoxic activities," J. Immunol. 154(8):3969–3974 (1995).

Lamm, "Long–term results of intravesical therapy for superficial bladder cancer," Urol. Clin. North Am. 19(3):573–580 (1992) (Abstract only).

Lee et al., "T helper 2–dominant antilymphoma immune response is associated with fatal outcome," Blood 90(4):1611–1617 (1997).

Leipner et al., "Systemic enzyme therapy in oncology: effect and mode of action," Drugs 59(4):769–780 (2000) (Abstract only).

Li et al., "Effects of direct current on dog liver: possible mechanisms for tumor electrochemical treatment," Bioelectromagnetics 18:2–7 (1997).

Li et al., "Cyclophosphamide given after active specific immunization augments antitumor immunity by modulation of Th1 commitment of CD4+ T cells," J. Surg. Oncol. 67:221–227 (1998).

Lowes et al., "T helper 1 cytokine mRNA is increased in spontaneously regressing primary melanomas," J. Invest. Dermatol. 108(6):914–919 (1997).

Lowin et al., "Cytolytic T–cell cytotoxicity is mediated through perforin and Fas lytic pathways," Nature 370:650–652 (1994).

Lucey et al., "Type 1 and type 2 cytokine dysregulation in human infectious, neoplastic, and inflammatory diseases," Clin. Microbiol. Rev. 9(4):532–562 (1996) (Abstract only).

Maeurer et al., "Host immune response in renal celll cancer: interleukin–4 (IL–4) and IL–10 mRNA are frequently detected in freshly collected tumor–infiltrating lymphocytes," Cancer Immunol. Immunother. 41(2):111–121 (1995) (Abstract only).

Mantovani, "The chemokine system: redundancy for robust outputs," Immunol. Today 20(6):254–257 (1999).

Mokyr et al., "Interleukin 2 requirement for the in vitro generation of antitumor cytotoxicity by thymocytes from melphalan–cured MOPC–315 tumor bearers," Cancer Res. 49(4):870–876 (1989) (Abstract only).

Mosmann et al., "Two types of murine helper T cell clone," J. Immunol. 136(7):2348–2357 (1986).

Negus et al., "Quantitative assessment of the leukocyte infiltrate in ovarian cancer and its relationship to the expression of C–C chemokines," Am. J. Pathol. 150(5):1723–1734 (1997) (Abstract only).

"New immunological paradigm, The," http://www.medcellbio.com/ accessed Sep. 11, 2000 (14 pages).

Oka et al., "An immunomodulatory arabinomannan extracted from mycobacterium tuberculosis, Z–100, restores the balance of Th1/Th2 cell responses in tumor bearing mice," Immunol. Lett. 70(2):109–117 (1999) (Abstract only).

Okamoto et al., "Local injection of OK432 can augment the Th1–type T–cell response in tumor–draining lymph node cells and increase their immunotherapeutical potential," Int. J. Cancer 70:598–605 (1997).

Onishi et al., "An assessment of the immunological environment based on intratumoral cytokine production in renal cell carcinoma," BJU Int. 83(4):488–492 (1999) (Abstract only).

Patard et al., "Immune response following intravesical bacillus Calmette–Guerin instillations in superficial bladder cancer: a review," Urol. Res. 26:155–159 (1998).

Pellegrini et al., "Disregulation in TH1 and TH2 subsets of CD4+ T cells in peripheral blood of colorectal cancer patients and involvement in cancer establishment and progression," Cancer Immunol. Immunother. 42:1–8 (1996).

Peterson et al., "Subcutaneous or oral administration of rhIL–11 modulates the contact hypersensitivity response," Cytokine 12(12):1769–1777 (2000).

Prescott et al., "Mechanisms of action of intravesical bacille Calmette–Guérin: local immune mechanisms," Clin. Infect. Dis. 31 (Suppl. 3):S91–S93 (2000).

Rayman, "The importance of selenium to human health," Lancet 356:233–241 (2000).

Romagnani, "Type 1 T helper and type 2 T helper cells: functions, regulation and rule in protection and disease," Int. J. Clin. Lab. Res. 21(2):152–158 (1991) (Abstract only).

Romagnani, "Lymphokine production by human T cells in disease states," Annu. Rev. Immunol. 12:227–157 (1994) (Abstract only).

Romagnani, "T–cell subsets (Th1 versus Th2)," Ann. Allergy, Asthma Immunol. 85:9–18 (2000).

Roussel et al., "High expression of adhesion molecules/activation markers with little interleukin–2, interferon γ, and tumor necrosis factor β gene activation in fresh tumor–infiltrating lymphocytes from lung adenocarcinoma," Cancer Immuno. Immunol. 41:1–9 (1995).

Roussel et al., "Predominance of a type 2 intratumoural immune response in fresh tumour–infiltrating lymphocytes from human gliomas," Clin. Exp. Immunol. 105:344–352 (1996).

Roussel et al., "Transendothelial migration induces rapid expression on neutrophils of granule–release VLA6 used for tissue infiltration," J. Leukoc. Biol. 62:356–362 (1997).

Rubin et al., "Characterization of the exogenous interleukin–2 requirements for the generation of enhanced antitumor cytotoxicity by thmocytes from low–dose melphalan–treated MOPC–315 tumor bearers,"Cancer Immunol. Immunothyer. 36(1):37–44 (1993) (Abstract only).

Ruzek et al., "Specific decrease of Th1–like activity in mice with plasma cell tumors," Int. Immunol. 7(7):1029–1035 (1995) (Abstract only).

Sadanaga et al., "Local secretion of IFN–gamma induces an antitumor response: comparison between T cells plus IL–2 and IFN–gamma transfected tumor cells," J. Immunother. 22(4):315–323 (1999) (Abstract only).

Saint et al., "Mechanisms of action of BCG: towards a new individualized therapeutic approach," Prog. Urol. 10(6):1118–1126 (2000) (Abstract only).

Sato et al., "Impaired production of Th1 cytokines and increased frequency of Th2 subsets in PBMC from advanced cancer patients," Anticancer Res. 18(5D):3951–3955 (1998) (Abstract only).

Shankar et al., "Zinc and immune function: the biological basis of altered resistance to infection," Am. J. Clin. Nutr. 68 (suppl):447S–463S (1998).

Singh et al., "The paradigm of Th1 and Th2 cytokines: its relevance to autoimmunity and allergy," Immunol. Res. 20(2):147–161 (1999) (Abstract only).

Sprietsma, "Modern diets and diseases: NO–zinc balance. Under Th1, zinc and nitrogen monoxide (NO) collectively protect against viruses, AIDS, autoimmunity, diabetes, allergies, asthma, infectious diseases, atherosclerosis and cancer," Med. Hypotheses 53(1):6–16 (1999) (Abstract only).

Sredni et al., "Predominance of TH1 response in tumor-bearing mice and cancer patients treated with AS101" J. Natl. Cancer Inst. 88(18):1276–1284 (Abstract only).

Stein et al., "Modulation of the cellular and humoral immune responses of tumor patients by mistletoe therapy," Eur. J. Med. Res. 3(4):194–202 (1998) (Abstract only).

Stephens et al., "Molecular characterisation of tumour infiltrating lymphocytes in oral squamous cell carcinoma," Cancer Immunol. Immunother. 46:34–40 (1998).

Straten et al., "Clonal T cell responses in tumor infiltrating lymphocytes from both regressive and progressive regions of primary human malignant melanoma," J. Clin. Invest. 98(2):279–284 (1996).

Tabata et al., "Th2 subset dominance among peripheral blood T lymphocytes in patients with digestive cancers," Am. J. Surg. 177(3):203–8 (1999) (Abstract only).

Takashi et al., "Possible factors affecting response to intravesical bacillus Calmette–Guerin (Tokyo 172 strain) therapy for carcinoma in situ of the bladder: a multivariate analysis," Int. Urol. Nephrol. 30(6):713–722 (1998) (Abstract only).

Takeuchi et al., "Th2–like response and antitumor effect of anti–interleukin–4 mAb in mice bearing renal cell carcinoma," Cancer Immunol. Immunother. 43(6):375–381 (1997) (Abstract only).

Tanaka et al., "Flow cytometric analysis of helper T cell subsets (Th1 and Th2) in healthy adults," Rinsho Byori 46(12):1247–1251 (1998) (Abstract only).

To et al., "Therapeutic efficacy of Th1 and Th2 L–selectin–CD4+ Tumor–reactive T cells," Laryngoscope 110(10):1648–1654 (2000).

Tsung et al., "Immune response against large tumors eradicated by treatment with cyclophosphamide and IL–12," J. Immunol. 160:1369–1377 (1998).

Weber et al., "Vitamin E and human health: rationale for determining recommended intake levels," Nutrition 13(5):450–460 (1997).

Whiteside et al., "Tumor–infiltrating lymphocytes: their phenotype, functions and clinical use," Cancer Immunol. Immunother. 39:15–21 (1994).

Winter et al., "Tumor regression after adoptive transfer of effector T cells is Independent of perforin or fas ligand (APO–1L/CD95L)," J. Immunol. 163:4462–4472 (1999).

Wong et al., "Cytokine profiles in spontaneously regressing basal cell carcinomas," Brit. J. Dermatol. 143:91–98 (2000).

Xiang et al., "Regression of engineered tumor cells secreting cytokines is related to a shift in host cytokine profile from type 2 to type 1," J. Interferon Cytokine Res. 20:349–354 (2000).

Xin et al., "Electrochemical treatment of lung cancer," Bioelectromagnetics 18:8–13 (1997).

Yamamura et al., "Local expression of antiinflammatory cytokines in cancer," J. Clin. Inv. 91:1005–1010 (1993).

* cited by examiner

THERAPEUTIC MODULATION OF THE TUMOR INFLAMMATORY RESPONSE

CROSS-REFERENCE TO RELATED APPLICATIONS

Not applicable

STATEMENT REGARDING FEDERALLY SPONSORED RESEARCH OR DEVELOPMENT

Not applicable

REFERENCE TO A MICROFICHE APPENDIX

Not applicable

BACKGROUND OF THE INVENTION

Human (and other vertebrate) immune responses comprise complex and intricately regulated sequences of events, involving cells of several different types. An immune response can be triggered when an antigen in a human body encounters an antigen-presenting cell (APC). The APC can capture the antigen and display a portion of it on its surface in a form that can be recognized by a helper T (Th) lymphocyte. Upon binding of a Th lymphocyte with the APC-displayed antigen, the Th lymphocyte can become activated. An activated Th lymphocyte promotes activation of lymphocytes of other types, the particular type(s) depending on the identity of the Th lymphocyte and the context in which the antigen is displayed by the APC. Various types of Th lymphocytes can, for example, promote activation of cytotoxic T cells or proliferation or differentiation of antigen-specific B cells. Th lymphocytes can activate other lymphocytes by secreting one or more polypeptide hormones designated cytokines. Th lymphocytes exhibit the CD4 antigen on their surface.

Functionally distinct types of Th cells have been described in humans. At least two types of Th cells have been characterized, based on the cytokines they produce. Type 1 Th cells (i.e., Th1 cells) can produce interleukin-2 (IL-2), interferon-gamma (IFN-g), and tumor necrosis factor-beta (TNF-b). Type 2 Th cells (i.e., Th2 cells) can produce IL-4, IL-5, IL-6, and IL-10.

Immune responses activated by Th1 cell activation (i.e., a 'type 1 immune response' or 'Th1-mediated response') are characterized by significant production of IFN-gamma and promotion of cytotoxic lymphocyte activity. Type 1 immune responses can be induced, for example, by the presence of bacteria in the human body. The cytotoxic lymphocytes activated in a Th1-mediated response are capable of recognizing and killing cells that display the Th1-activating antigen on their surface. Thus, induction of a type 1 immune response can lead to elimination from the body of antigen-bearing cells. Excessive or otherwise inappropriate induction of a type 1 immune response can cause damage to normal (i.e., non-diseased tissues) in a human.

Immune responses activated by Th2 cell activation (i.e., a 'type 2 immune response' or 'Th2-mediated response') are characterized by significant production of IL-4 and promotion of humoral immunity (e.g., production of immunoglobulins, particularly including IgE). Type 2 immune responses are commonly induced in response to chronic infections (e.g., parasitic infections), and tend to inhibit, prevent, or reverse type 1 immune responses. Type 2 immune responses will normally eliminate a pathogen from the body, and can thereby inhibit further infection by an infectious agent. However, type 2 immune responses generally do not eliminate all pathogen-infected or diseased cells from the body. Thus, cells which exhibit the antigen that induced the type 2 immune response may persist chronically in the body. This occurs particularly when antigen-bearing cells (e.g., virus-infected cells or tumor cells) induce inappropriate activation of a type 2 immune response, which can facilitate persistence of the antigen-bearing cells in a human body.

Inflammation is a normal localized immune response to invasion or injury caused by an infectious agent (e.g., a bacterium) or by a tumor. In a process analogous to the manner in which blood flow can increase the supply of glucose and oxygen to active muscle tissue during a period of exercise, an inflammatory response can increase the supply of elements of the immune system at a local disease (e.g., infection or tumor) site in order to mount an effective defensive immune response. An effective inflammatory response can be characterized by at least six events:

i) release of antigens from diseased or pathological cells at the disease site and secretion of chemotactic factors at the injured site;

ii) infiltration of the disease site by cells of the immune system;

iii) polarized type I or type II activation of the immune cells by the antigens released at the site;

iv) amplification of the inflammatory response over time, at least for a limited period;

v) elimination of the diseased or pathological cells by immune cells; and vi) conversion of activated immune cells into memory cells which are capable of providing long-term protection against the antigen or antigen-bearing cells.

Cancer is one of the foremost causes of mortality and morbidity among humans. Many cancers are manifested by the existence of tumors, which are clumps or masses of cancer cells. In the past, cancer cells were generally believed to be non-immunogenic, since they are derived from autologous (i.e., 'self') tissue, which normally does not induce an immune response. However, tumor-reactive lymphocytes can be isolated from patients afflicted with many types of cancer (Lee et al., 1997, Blood 90:1611–1617).

A significant portion of tumor mass is made up of lymphocytes. These cells, designated tumor-infiltrating lymphocytes (TILs), typically produce cytokines (e.g., IL-4) that are characteristic of a type 2 inflammatory response (Roussel et al., 1996, Clin. Exp. Immunol. 105:344–352). It has been postulated that predominance of type 2 TILs support a type 2 inflammation in tumors that inhibits tumoricidal cytotoxic immune responses. It has furthermore been suggested that modulation of the type of immune response exhibited by TILs can have anti-cancer therapeutic effects (Gorelik et al., 1994, Cancer Immunol. Immunother. 39:117–126; Pellegrini et al., 1996, Cancer Immunol. Immunother. 42:1–8; Goedegebuure et al., 1997, Cell Immunol. 175:150–156; Fujimoto et al., 1997, J. Immunol. 158:5619–5626; Okamoto et al., 1997, Int. J. Cancer 70:598–605; Stein et al., 1998, Eur. J. Med. Res. 3:194–202; Li et al., 1998, J. Surg. Oncol. 67:221–227). However, despite this recent understanding regarding both types of inflammatory response, no course of treatment has previously been identified whereby a type 2 inflammatory response (i.e., one conducive to tumor survival or growth) can be converted to or overcome by a type 1 inflammatory response (i.e., one in which tumor growth slows or halts and tumor regression is enhanced).

Current cancer therapies (e.g., surgery, radiotherapy, and chemotherapy) are relatively inefficient, and have very debilitating side effects that lead to relapses and death. In view of the overwhelming toll of human mortality and morbidity associated with cancer, an urgent need remains for therapeutic compositions, kits, and methods which can slow or reverse tumor progression in humans while reducing morbidity and offering protection against tumor relapse. The present invention satisfies this need, at least in part, by providing therapeutic compositions, kits, and methods which can be used to reliably treat a variety of human cancers, reduce treatment-related morbidity (relative to prior art therapeutic methods), and offer protection against tumor relapse.

BRIEF SUMMARY OF THE INVENTION

The invention relates to a method of alleviating a tumor in a human patient. The method comprises locally administering to the tumor (i) an antigen-releasing agent, (ii) a leukocyte attractant, and (iii) interferon-gamma (IFN-g) and a second type 1 inflammatory response-(IR1-)promoting agent (e.g., one of linterleukin-2 (IL-2), interleukin-12 (IL-12), tumor necrosis factor-alpha (TNF-a), and tumor necrosis factor-beta (TNF-b)).

The antigen-releasing agent induces release of one or more tumor antigens from cells of the tumor, and can, for example, be one of a proteolytic enzyme, an apoptosis-inducing agent, electrical current, a strong acid, and a strong base. The leukocyte attractant induces leukocytes to infiltrate the tumor. Together, the agents administered to the tumor induce a type 1 inflammatory response in the tumor and alleviate the tumor (i.e., cause it to shrink or disappear). An added benefit of this therapeutic method is that the incidence of tumor recurrence can be decreased, relative to other tumor alleviation methods.

In one embodiment, the method further comprises locally administering to the tumor a type 1 lymphocyte attractant (e.g., one of RANTES, IP-10, and Mig), in order to sustain the type 1 inflammatory response. The type 1 inflammatory response can also (or instead) be sustained by administering autologous leukocytes to the patient. These leukocytes can be isolated from the patient, expanded ex vivo, induced to differentiate, and returned to the patient, preferably by local administration at the tumor site In order to reduce recurrence of the tumor, a memory cell-inducing agent (interleukin-15 (IL-15) or interferon-alpha (IFN-a)) can be administered to the patient in order to enhance production of anti-tumor type 1 immune memory cells. When used, the memory cell-inducing agent is preferably administered locally to the tumor site after most (e.g., 90%) of the tumor mass has disappeared, but before the tumor has been completely ablated.

The therapeutic method can further comprise supplementing the patient's nutrition with a nutrient such as a vitamin (e.g., one or more of vitamins A, B, C, D, and E) or a mineral (e.g., one or more of selenium, zinc, calcium, magnesium, iron, and copper).

The invention also includes compositions useful in performing a tumor therapeutic method described herein. For example, such a composition can comprise IFN-g and a second IR1-promoting agent. Local administration of the composition to a tumor induces a type 1 inflammatory response in the tumor, and the tumor is thereby alleviated. The composition can further comprise one or more of a leukocyte attractant, an antigen-releasing agent, and a pharmaceutically acceptable carrier.

The invention also includes a kit for alleviating a tumor in a human patient. The kit can comprise one or more of the agents used in the methods described herein, equipment and devices used in those methods, and an instructional material which describes one or more of the methods.

DETAILED DESCRIPTION OF THE INVENTION

The invention relates to compositions, kits, and methods for alleviation of cancer in human patients. The invention is based on inducing a type 1 inflammatory response at the site of a tumor. Induction (or enhancement) of a type 1 inflammatory response at a tumor site (i.e., within and near the margins of a tumor) can cause the tumor to shrink or disappear, reduce the invasiveness or metastatic capacity of the tumor, and enhance production of immune memory cells which specifically recognize tumor tissue and inhibit or prevent relapse (i.e., recurrence) of the tumor.

Although the desirability of exchanging a type 1 immune response in tumor tissue in place of the normally-prevalent type 2 response is becoming better understood, there is presently no treatment for reliably establishing a type 1 immune response in tumor tissue. The present invention overcomes the deficiencies of the prior art by providing therapeutic compositions, kits, and methods which can reliably be used to activate Th1 cells in and around tumor tissue, with the result that tumor-cytotoxic inflammation is induced in the tumor, leading to its regression or elimination.

Prior art methods of inducing tumor cell death include administration of agents which are cytotoxic to tumor cells, but which either exhibit lesser cytotoxicity with respect to non-tumor cells or are selectively delivered to tumor cells. Although these methods have exhibited limited success at limiting the size and rate of progression of tumors, at least for limited periods, many of these methods also exhibit a critical drawback that limits their effectiveness. Delivery of a cytotoxic agent (e.g., radiation or a cytotoxic chemical compound) to a tumor can kill not only tumor cells, but also any non-tumor cells which are present in the tumor. This cytotoxicity can be caused by the direct effect of the agent on the non-tumor cells, by a 'by-stander' effect wherein the agent induces localized cytotoxicity that is not specific for tumor cells (e.g., by release of a cytotoxin such as ricin from an agent intended to deliver the cytotoxin specifically to tumor cells), or by other mechanisms. Tumors normally comprise a significant number of leukocytes which, if appropriately activated, can induce tumor cell death and lead to tumor regression. Many anti-tumor cytotoxic agents kill these lymphocytes in addition to tumor cells. Thus, although many prior art anti-tumor agents kill significant numbers of tumor cells, the agents also kill significant numbers of leukocytes in the tumor. Elimination or inactivation of these tumors reduces the body's ability to marshal its cytotoxic immune resources to combat the tumor. The net effect of anti-tumor treatment using many of these prior art anti-tumor agents is temporary reduction in tumor mass without enhancement of the body's ability to destroy the tumor remnants or prevent recurrence of the tumor. As a result, tumor recurrence frequently occurs following prior art anti-tumor treatment methods.

The methods described in this specification can be distinguished from prior art anti-tumor therapeutic methods in several ways. For example, the methods described herein enhance activity and proliferation of the body's anti-tumor cytotoxic immune cells within and in the immediate vicinity of the tumor, rather than killing these cells as in prior art methods. Furthermore, by enhancing activity and proliferation of anti-tumor immune cells, the methods described herein can inhibit or prevent recurrence of the tumor in that patient's body.

The anti-tumor therapeutic methods described herein can be outlined as follows. Enzymes or other compounds which cause release of antigens from tumor cells (and which preferably also induce tumor cell death) are delivered locally to a tumor. These compounds are selected such that they are not cytotoxic with respect to lymphocytes (or at least less cytotoxic with respect to lymphocytes than with regard to tumor cells). TILs are attracted to the tumor site by local administration of one or more chemokines to tumor tissue. Local administration of type I lymphokines to the tumor polarizes the TILs to exhibit a type 1 inflammatory response, leading to tumor tissue destruction. Sustained amplification of the type 1 inflammatory response can be effected by repeated local delivery of the type 1-polarizing cytokines to the tumor site. The net effect of this treatment is that the body's own immune defenses are mobilized for destruction of the tumor. Continued survival of type 1-polarized lymphocytes, converted into memory cells, in the patient's body can prevent recurrence of the tumor at the same site or at a different body location. These lymphocytes can also travel to and destroy related tumors which may exist in the patient's body (e.g., by metastasis of cells from the original tumor).

These methods, and compositions and kits for performing them, are set forth in greater detail in the following sections.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

A "tumor" refers to a solid or semi-solid mass of tissue comprising cells which exhibit uncontrolled growth characteristic of cancer. Tumors include both benign tumors (i.e., those which do not appear to be invading surrounding tissues or metastasizing to other body sites) and malignant (i.e., non-benign) tumors.

"Co-administration" of two or more agents means administration of the agents sufficiently close in time that the periods of significant activity of each of the agents in vivo overlaps. By way of example, co-administration includes administration of a first and a second agent sufficiently close in time that the level of activity, in vivo, that is attributable to the first agent is more than half its maximum post-administration level at a period of time when the level of activity, in vivo, that is attributable to the second agent is more than half its maximum post-administration level. Co-administered agents can be administered in the form of a single composition comprising each agent, in the form of individual agent preparations, or (i.e., when there are more than two agents) in combinations of such forms.

Description

Tumorigenesis is a largely continuous occurrence in animals such as humans. Every day, millions of cell divisions occur in a human, and mutations and other genetic lesions inevitably occur in at least some of these divisions, leading to generation of cells which exhibit uncontrolled growth (i.e., cancer cells). Recognition and destruction of cancer cells are among the normal functions of the human immune system. When appropriately activated, cells of the type 1 immune response (including, for example, cytotoxic T cells) are capable of specifically destroying cells which exhibit abnormal cell surface markers (e.g., cancerous or virus-infected cells). However, survival of cancer cells is sometimes promoted by activation of cells of the type 2 immune response, which are normally associated with inactivation of parasitic or chronic infective agents, but which are not normally associated with tumorotoxicity. The type 2 immune response can sometimes be induced by the cancerous cells themselves, such as when the cancerous cells secrete factors which promote induction of the type 2 immune response.

Among the characteristics of the type 2 immune response is that type 1 inflammatory responses are inhibited when it occurs. Because tumoricidal cytotoxicity is associated with the type 1 inflammatory response, but not with the type 2 immune response, the type 2 immune state can prolong survival of tumor tissue and permit that tissue to evade the patient's normal immune defenses.

The anti-cancer therapeutic method described in this specification involves altering the type 2 immune response which normally occurs in tumor tissue such that a type 1 inflammatory response takes over (i.e., type 1 inflammation is initiated or de-repressed). Cells associated with the type 1 inflammatory response recognize and kill tumor cells, thereby achieving tumor reduction (or even elimination) in the absence of the often debilitating or disfiguring side effects associated with administration of prior art anti-tumor agents.

In a preferred embodiment, the treatment method comprises three elements, as set forth in the three ensuing paragraphs. Although the elements are designated 'first,' 'second,' and 'third,' the actions corresponding to these elements need not be performed in this sequential order (although, in a preferred embodiment, the actions corresponding to the first element are performed prior to {e.g., at least two hours prior to} the actions corresponding to the second and third elements).

First, one or more agents (e.g., tumor de-bulking agents such as proteases or mixtures of proteases) are administered directly to the tumor tissue (e.g., by injection into the tumor at one or more sites) in order to cause release of tumor antigens from tumor cells. Without being bound by any particular theory of operation, it is believed that release of antigens from tumor cells permits those antigens (e.g., fragments of tumor cell surface proteins) to interact with immune cells in ways that are not possible when the antigens remain part of a tumor cell. Release of tumor antigens from tumor cells facilitates induction of immune responses which are specific for the tumor cells.

Second, TILs are recruited to the tumor site by local administration of one or more TIL chemoattractants. TILs that are recruited to the tumor site can be activated to secrete chemokines which attract more TILs, induce the TILs to exhibit a type 1 inflammatory response, or both.

Third, leukocytes present at (or recruited to) the tumor site are induced to exhibit a type 1 inflammatory response by locally administering two or more type 1 inflammatory response promoting agents ("IR1-promoting agents") including interferon-gamma ("IFN-g") with others such as linterleukin-2 ("IL-2"), and tumor necrosis factor beta ("TNF-b") to the tumor tissue. The IR1-promoting agents are preferably administered together in a single composition; however, they can be administered separately, but closely in time (e.g., seconds or minutes up to a few hours apart). The IR1-promoting agents can be locally administered to the tumor, for example, by injecting them into one or more sites in the tumor, peritumorally, or both. Preferably, the IR1-promoting agents are injected into two or more sites in the tumor, the sites spaced approximately equally apart in the tumor mass.

In the presence of two or more of these agents, TILs exhibit characteristics of a type 1 inflammatory response, such as the ability to kill tumor cells and virus-infected cells. Such TILs can destroy tumor tissue, leading to shrinkage, or even disappearance, of the tumor from the patient's body and alleviation of tumor-related symptoms (e.g., pain, weight loss, nausea, exhaustion, and symptoms associated with the presence of a tumor at a particular body location).

Although the tumor treatment method can include only these three steps, preferred embodiments of the method include one or more of three additional steps, which are designated the fourth, fifth, and sixth steps in the ensuing three paragraphs.

Fourth, the effectiveness (i.e., sustained potency) of the treatment can be enhanced by amplifying the type 1 inflammatory response induced in and/or around the tumor tissue. This can be achieved, in one embodiment, by additional (e.g., sustained or repetitive) local administration of the same or different IR1-promoting agents to the tumor tissue or the tumor site. Alternatively, or in addition, autologous lymphocytes can be provided to or near the tumor site, in order to provide a greater pool of lymphocytes from which TILs can be generated or separated. The autologous lymphocytes can have been induced to proliferate ex vivo, in order to enhance the number of cells available for administration to the tumor site. The additional lymphocytes can also have been induced to differentiate into Th1-VLA6$^+$ or Th1-CD49f$^+$ cells by treating them, ex vivo, with one or more IR1-promoting agents.

Fifth, generation, proliferation, or both, of immune memory cells can be induced by injecting a memory cell-inducing agent (e.g., interferon-alpha {"IFN-a"} or interleukin-15 {IL-15}) at or near the tumor site at one or more steps of the treatment. Immune memory cells (e.g., activated B or T lymphocytes) are normally formed in the presence of an antigen, and normally are able to rapidly differentiate to form type 1 and type 2 immune cells upon re-exposure to the antigen. However, during a type 2 immune response, formation of type 1 immune memory cells can be inhibited and their differentiation or activation in response to the presence of the antigen can be inhibited. Formation of these type 1 memory cells is preferably enhanced during the period of type 1 inflammatory response brought about by the other steps of the treatment disclosed herein, resulting in formation of type 1 memory cells which can rapidly respond to recurrence of the tumor at the same or a different body site.

Sixth, the effectiveness of the anti-tumor treatment disclosed herein can be enhanced by enhancing the patient's general state of health, and particularly by enhancing the state of the patient's immune system. Nutritional supplementation methods are known in the art, and preferred regimens are described herein.

In the following sections, particular aspects of these six steps are disclosed. The anti-tumor treatment includes at least the steps of enhancing tumor antigen release, inducing tumor infiltration by lymphocytes, and induction of a type 1 inflammatory response. Of course, two or more of these steps can be combined, although the antigen-release step preferably precedes the others by a period of at least several hours (i.e., in order to generate a gradient of tumor antigen having its focus at the tumor site). One or more of the fourth, fifth, and sixth steps described above (and preferably all three) can be included in the method. The sixth step can be performed at any time during the method, and is preferably performed throughout. The fourth and fifth steps preferably follow the antigen-release step by a period of at least several hours.

Enhancing Tumor Antigen Release

The method includes inducing release of antigens from tumor cells. Many methods which induce antigen release are also associated with significant cytotoxicity. Thus, the antigen release step can effect de-bulking of the tumor as well. So long as more (preferably significantly more) tumor cells than lymphocytes are killed, the de-bulking can enhance or speed the anti-tumor treatment by reducing the tumor burden in the patient. Tumor de-bulking can be achieved by administering a tumor de-bulking agent to the tumor in order to cause death of at least a fraction of tumor cells and release of tumor antigens from the killed tumor cells. The antigen-release-inducing agent can be administered locally to the tumor tissue, systemically, or in any other manner in which the agent is brought into contact with the tumor tissue.

The antigen-release-inducing agent is preferably one which exhibits relatively little or no cytotoxicity with regard to leukocytes, particularly with regard to TILs. Examples of suitable antigen-release-inducing agents include compositions comprising one or more de-bulking agents, which include proteolytic enzymes such as trypsin, chymotrypsin, pepsin, and collagenase, apoptosis-inducing agents such as alkylphospholipids (e.g., alkylphosphocholines such as hexadecylphosphocholine or edelfosine), electrical current (e.g., delivered by way of electrodes inserted into tumor tissue), and strong acids and bases (e.g., concentrated solutions of sodium and potassium hydroxides and hydrochloric acid). The agent is administered locally to the tumor tissue (e.g., by topical application to the tumor tissue or by intratumoral and/or peri-tumoral injection) in order to decrease damage to non-tumor tissues.

Surgical tumor disruption and radiative tumor disruption methods can be used to induce release of antigens from tumor cells. However, these methods are not preferred, owing to their relative non-specificity with respect to killing tumor cells and lymphocytes. Of course, it can be possible to overcome this limitation by providing lymphocytes to the tumor site from an extracorporeal source (e.g., autologous lymphocytes which have been induced to proliferate, differentiate, or both, ex vivo).

The following four paragraphs describe examples of methods of inducing release of antigens from a tumor located in a patient's body.

An aqueous composition comprising one or more proteases (e.g., one or more of trypsin, chymotrypsin, pepsin, and collagenase) is prepared, wherein the concentration of each protease is about 2,000 to 10,000 units per cubic centimeter of tumor volume to be targeted. An aliquot of this solution representing from about $\frac{1}{50}$ to $\frac{1}{100}$ of the volume of the tumor to be affected is injected into the tumor. For example, about 100 microliters of a suspension of several proteases, each having a concentration of about 50,000 units per milliliter can be injected into a tumor having a volume of about 10 milliliters. This solution is preferably injected into several locations in the same tumor, in order to distribute the antigen-releasing and/or tumor-de-bulking effects throughout the tumor mass. Using this treatment, about 10–20% of the tumor can be expected to be digested (i.e., about 10–20% of tumor cells will be killed). Of course, other concentrations and combinations of enzyme can be used.

In another embodiment, antigen release from a tumor is induced by injecting a solution of one or more alkylphosphocholines into the tumor mass, preferably at spatially distinct locations. Alkylphosphocholines are phospholipids which have structural similarity to naturally-occurring cell membrane phospholipids. Alkylphosphocholines such as hexadecylphosphocholine and edelfosine (1-O-octadecyl-2-

O-methyl-rac-glycero-3-phosphocholine) are relatively non-toxic with regard to lymphocytes, but can induce disruption (i.e., apoptosis) of tumor cells, thereby effecting antigen release. A suspension containing about 50–250 milligrams of each alkylphosphocholine per milliliter of tumor volume can be prepared, and an aliquot having a volume of about 1/50 to 1/100 the tumor volume can be injected. For example, 200 microliters of a suspension comprising 25% (w/v) hexadecylphosphocholine or edelfosine can be injected into a tumor having a volume of about 10 milliliters. The treatment described in this paragraph can be expected to disrupt about 10–20% of the tumor (i.e., to induce apoptosis of 10–20% of tumor cells).

In another embodiment, release of antigens from tumor cells can be induced by applying electrical potential across a portion of the tumor (i.e., by passing electrical current through a portion of the tumor). Electrochemical tumor disruption can be effected by inserting an electrode having a polarity (e.g., an anode) in one portion of a tumor mass, inserting an electrode having the opposite polarity (e.g., a cathode) in another portion of the tumor mass, and applying an electrical potential across the electrodes. Of course, multiple electrodes of each type can be used, so long as there is at least one electrode having a polarity opposite to that of another electrode. For example, an anode having a diameter of about 0.5 millimeter can be inserted in about the center of a tumor mass, and multiple cathodes can be inserted into the periphery of the tumor mass, about 3 centimeters apart from each other. A direct current potential of about 5–10 Volts is applied between the anode and cathodes, and about 40–100 milliamperes of current are delivered for a period of about 1–2 hours. The total charge delivered to the tumor during this period is estimated to be about 60–80 Coulombs per cubic centimeter of tumor. This treatment can be expected to induce tumor tissue destruction within about 3 centimeters from each electrode.

Disruption of tumor tissue and release of tumor antigens can also be effected by direct administration to tumor tissue of a solution of concentrated acid or base. For example, a 10 molar solution of hydrochloric acid or a 10 molar solution of sodium hydroxide can be administered intra-tumorally. An aliquot of either of these solutions equal in volume to about 1/50 to 1/100 of the tumor volume can be injected (for example, 100 microliters of one of these solutions can be injected into a tumor having a volume of 10 milliliters). The solution is preferably injected into two or more spatially distinct locations in the tumor mass, although a single injection can be used for small tumors. Treatment as described in this paragraph can be expected to induce death of about 10–20% of tumor cells, and the concentration or identity of the acid or base can be adjusted to effect this level of tumor cell killing.

Inducing Tumor Infiltration by Lymphocytes

The anti-tumor therapeutic method includes a step wherein leukocytes are attracted to the tumor site, or into the tumor itself. Recruitment of leukocytes at a particular location can also be effected by causing leukocytes that are already at the location to proliferate. It is known in the art that leukocytes of particular types can be attracted to a location in a body (or in vitro) by the existence of one or more particular chemokines at the location. Of course the particular types of leukocytes vary with the particular chemokines. For example, monocytes can be attracted to a site by the presence of MCP-1, MCP-2, MCP-3, or MCP-4. T cells are attracted by RANTES, IP-10, or Mig. Eosinophils can be attracted by the presence of eotaxin at a body location. Furthermore, recruitment of type 1 inflammatory cells can be enhanced by inducing proliferation or activation of the cells at the site. For example, IL-2 is known to induce proliferation of lymphocytes which exhibit the CD4 antigen (including Th1 lymphocytes) and to induce activation of lymphocytes which exhibit the CD8 antigen (e.g., cytotoxic T lymphocytes).

Leukocyte infiltration into a tumor is preferably induced following a period of several (e.g., 6–8) hours following induction of tumor antigen release. Waiting for this period prior to inducing leukocyte infiltration permits conditions used to disrupt tumor cells, or induce antigen release therefrom, to dissipate. This period also provides time for a gradient of tumor antigen to develop having the tumor at its most concentrated location. Formation of such a gradient can enhance the ability of lymphocytes and macrophages to localize specifically within the tumor.

One embodiment of a method by which infiltration of lymphocytes into a tumor is induced is as follows. A suspension comprising IFN-g and TNF-a is prepared, comprising about 20–100 units per milliliter of tumor volume of IFN-g and about 100–500 units per milliliter of tumor volume of TNF-a. The suspension further comprises IP-10 and Mig, each at a concentration of about 1–100 nanograms per milliliter of tumor volume. An aliquot of this suspension is administered intra-tumorally, the volume of the aliquot being approximately 1/50 to 1/100 the volume of the tumor. The aliquot is preferably administered by injection into one or more sites within the tumor, multiple sites preferably being approximately equidistant from one another. Injection of this suspension activates monocytes such that they produce monocyte chemoattractants and also attracts TILs to the tumor. In some instances, IP-10, Mig, or both, can be omitted from the suspension, because these TIL chemoattractants are normally produced by activated monocytes (which are attracted to the tumor site by IFN-g and TNF-a). The suspension can be repetitively administered to the tumor, or administered in a sustained-release formulation; however, repetitive and sustained administration will often be unnecessary, owing to the self-sustaining nature of the type 1 inflammatory response induced by attracting monocytes to the tumor site (i.e., the monocytes attract more monocytes and TILs).

In another embodiment, granulocytes (e.g., neutrophils and basophils) are attracted to the tumor site by including one or more granulocyte-attractive agents in the suspension of chemokines that is administered to the tumor. Examples of such agents include IL-8, granulocyte chemotactic protein-2 (GCP-2), growth-related oncogens 1, 2, and 3 (GROs), neutrophil-activating protein 2 (NAP-2), and others known in the art. The desirability of attracting granulocytes to a tumor can depend on the type of tumor being treated. For example, some tumors (e.g., certain brain tumors, such as gliomas) do not form solid tissue masses, but instead have a gelatinous consistency. In gelatinous tumors, granulocytes can enhance inducement, endurance, or both, of a type 1 inflammatory response in the tumor tissue, presumably attributable to cytotoxic factor exhibited by granulocytes. Thus, it can be preferred to include administration of a granulocyte-attracting chemokine in a composition, kit, or method for treating a semi-solid tumor.

In addition, it is recognized that certain chemokines can be more conveniently provided to certain tissues than others. For example, the chemokine designated neurotactin (sometimes designated fractalkine or type 1 membrane protein) can be administered to brain tissue (i.e., for treatment of brain tumors).

The effectiveness of numerous individual chemokines for inducing infiltration of lymphocytes into tissues of various types is known, although not all of these characteristics are replicated in this specification.

Initiation of the type I inflammatory response can, alternatively, be achieved or supplemented by injecting another inflammation-inducing agent into the tumor mass. For example, modified bacteria (e.g., Bacillus Calmest-Guerin), lipopolysaccharides, or mild tumor-de-bulking or tumor-antigen-releasing agents can be used to induce inflammation that will attract monocytes to the site. Once attracted to the site, the monocytes can secrete Th1-attracting lymphokines. Because it is preferable to achieve rapid and efficient induction of a type 1 inflammatory response, administration of IP-10, Mig, or (preferably) both, is the preferred method of inducing inflammation.

Inducing a Type 1 Inflammatory Response

The anti-tumor therapeutic methods described in this specification also include a step in which the lymphocytes present within a tumor or at the tumor site are induced to exhibit a phenotype and functional properties characteristic of a type 1 inflammatory response. Activation of Th1 cells and T cytotoxicl (Tc-1) cells which have cell surface receptors that bind specifically with tumor antigens is desirable, and contributes to tumor cell cytotoxicity. In some embodiments of the method, granulocytes can also be activated such that they contribute to the type 1 immune response and contribute to tumor cell cytotoxicity.

Promotion of a type 1 immune response within or in the vicinity of a tumor can be achieved by local administration of lymphokines which are normally produced by lymphocytes associated with a type 1 immune response. For example, a suspension of IL-2, IFN-g, and TNF-b can be administered in order to achieve this effect. The suspension can also comprise TNF-a and IL-12. Any combination of these five lymphokines can be used. However, the combination of IL-2, IFN-g, and TNF-b is preferred, because it has been discovered that this combination exhibits better synergy and permits use of lower doses of each of the three agents. For example, one useful suspension comprises 10–100 units of IL-2 per milliliter of tumor volume, 100–1000 units of IFN-g per milliliter of tumor volume, and 50–500 units of TNF-b per milliliter of tumor volume. An aliquot of this suspension having a volume from 1/50 to 1/100 of the volume of the tumor to be treated is administered intra-tumorally, at one or more sites in the tumor mass. The lymphokine suspension should be administered every 48–72 hours until the tumor mass becomes very small (e.g., less than 5% its original size) or undetectable (e.g., using digital imaging techniques such as CAT scanning). Alternatively, the lymphokine composition can be delivered in a sustained release form, so that fewer repetitions of the administration are necessary. For example, slowly-dissolving rods comprising a biodegradable matrix (e.g., PLGA) having the lymphokine(s) sequestered therein can be used to effect delivery over a period of days or weeks.

Sustained Promotion of Type 1 Inflammatory Response

The effectiveness of the anti-tumor therapeutic method described in this specification can be enhanced by multiple (or sustained or continuous) local administration of one or more chemokines, followed by local administration of cytokines normally associated with a type 1 immune response. The effectiveness of the method can also be enhanced by single or multiple provision of leukocytes expanded or differentiated in vitro.

For example, Mig and IP-10, two chemokines that attract both Th1 and Tc1 lymphocytes are prepared in a suspension comprising 10–500 nanograms each per milliliter. This suspension can be injected into the tumor less than about an hour before administering autologous lymphocytes that have been expanded or differentiated in vitro. Providing these chemokines to diffuse in the tumor before providing the lymphocytes enhances infiltration of the lymphocytes into the tumor. Without being bound by any particular theory of operation, this enhancement of infiltration is believed to be attributable to the ability of these chemokines to activate avidity of the beta-1 integrin receptors on lymphocytes, causing them to migrate along the chemokine gradient. Thus, other compounds having this same effect can be used in place of these chemokines.

Lymphocyte populations can also be expanded and differentiated in vitro using known methods. Preferably, the lymphocytes used in such in vitro procedures are obtained from the patient to whom they expanded or differentiated lymphocytes are to be administered, so that the patient's immune system will not reject the lymphocytes and so that the administered lymphocytes will not attack healthy (e.g., non-tumor) patient tissues. Also, the lymphocytes should be treated (e.g., by exposing them to IL-12) in order to enhance expression of VLA-6, an integrin necessary for tumor infiltration (Roussel et al., 1997, J. Leuk. Biol. 62:356).

Expansion of blood lymphocytes can be achieved by collecting lymphocytes from a patient. These lymphocytes will normally comprise a mixture of Th1-Tc1 and Th2-Tc2 cells. The lymphocytes are maintained for five days in the presence of a low dose if IL-2 (e.g., 10–25 units per milliliter of medium) and a low dose (e.g., 10–100 units per milliliter of medium) of either IL-12 or IFN-g to promote Th1-Tc1 expansion. Following this incubation, non-adherent cells are collected and expanded from 0.25 million cells per milliliter to 1.0 million cells per milliliter in the same medium. The cells are expanded several fold over the course of about 10 days (e.g., in AIM-V serum-free medium {GIBCO} in the presence of the same cytokines). Differentiation of the cells is achieved by adding 10–100 units per milliliter of IL-12 or IFN-a to the medium for 16–24 hours prior to injection of the cells into the patient. This IL-12 (or IFN-a) treatment enhances expression of integrin VLA-6. The resulting expanded type 1 cells are infused peri-tumorally into the patient's body at a ratio of about 10 million to 100 million cells per milliliter of targeted tumor. The cells are infused or injected at or near the tumor site (e.g., within a void in the tumor mass formed by a tumor-antigen-release enhancing agent, such as electrical current or a strong acid, or at a plurality of sites surrounding the tumor mass).

Alternatively, lymphocytes can be expanded by incubating blood lymphocytes obtained from a patient with T cell receptor-specific antibodies fixed to beads (e.g., polyacrylamide beads). After rinsing the beads, they can be suspended in a medium, at a concentration of about 1 million beads per million cells, in a medium such as AIM-V in the presence of 10–100 units per milliliter IL-12 or IFN-g. Cells in the suspension are expanded several fold over the course of about 10 days. Prior to injecting the cells into the patient, the cells are separated from the beads and differentiated by exposing them to 10–100 units per milliliter IFN-a for 16–24 hours in order to enhance expression of VLA-6. The resulting expanded type 1 cells are infused peri-tumorally into the patient's body at a ratio of about 10 million to 100 million cells per milliliter of targeted tumor. The cells are infused or injected at or near the tumor site.

It is understood that in certain patients (e.g., those who mount an aggressive immune response to the tumor following the initial induction of type 1 inflammation and those who are afflicted with only small tumors), promotion of a sustained type 1 inflammatory response will be unnecessary.

Thus, the anti-tumor method described herein need not include a step in which promotion of such inflammation is sustained. Omission of this step may adversely affect production of immune memory cells, resulting in a less aggressive immune response in the event the tumor recurs. Thus, this step is preferably not omitted.

Generation and Proliferation of Immune Memory Cells

The human immune system will normally produce immune memory cells during the course of a reaction to a pathogen-infected or tumor cell when a type 1 inflammatory response occurs in association with those cells. Production of immune memory cells can be insufficient to achieve an effective immune response upon recurrence of the tumor. However, generation and proliferation of immune memory cells can be enhanced during a type 1 inflammatory response by administering one or more appropriate agents (i.e., "memory cell-inducing agents" such as IL-15 and IFN-a) to the patient, preferably, at the site of inflammatory response.

In one embodiment, production of immune memory cells is enhanced by administering about 100–1000 units per milliliter of tumor volume of IL-15 at the tumor site. Administration of IL-15 decreases the intensity of the inflammatory response and promotes conversion of activated T cells into memory T cells. These memory T cells endure in the body and perform a 'patrolling' function for many years. Further growth of the tumor at the treatment site, or growth of the tumor at a distant site, can induce a rapid anti-tumor immune response, thereby providing protection against recurrence of the tumor in the patient.

Of course, the anti-tumor treatment described herein can be performed without enhancing generation and proliferation of immune memory cells. However, owing to the long-term protective effect that can be achieved if this step is performed, the method preferably includes a step of this type.

Patient Nutrition

In order to maximize the effectiveness of the anti-tumor treatment, the general state of health of the patient's immune system should be supported to the greatest extent possible, so that the treatment is not limited by immunodeficiencies not related to the patient's tumor load. For example, the patients nutritional intake should be monitored, and supplemented if necessary, in order to ensure that nutritional deficiencies do not limit the capacity of the patient's immune cells to mount a type 1 inflammatory response. Examples of suitable nutritional regimens have been described (e.g., Bendich, 1997, Nutrition, 13:154–155; Weber et al., 1997, Nutrition 13:450–460; Rayman, 2000, Lancet 356:233–241; Anura et al., 1998, Am. J. Clin. Nutr. 68(suppl):447S–463S). It is believed that particular nutritional requirements for which patient compliance should be monitored include a daily uptake of vitamin C (200–400 milligrams), vitamin E (200–400 IU), selenium (200–400 micrograms), and zinc (15–100 milligrams). In addition, a multi-vitamin formula that includes the vitamins A, B, and D, and minerals such as calcium, magnesium, iron, copper, and trace amounts of other vitamins and minerals normally found in a well-equilibrated formula should be included in the patient's daily diet in order to enhance the patient's immune function.

Compositions

The invention includes compositions which are useful in performance of the methods described herein. Such compositions can include individual agents which are packaged in a form convenient for one or more of storage, transportation, and administration to human patients. These compositions can also include multiple agents which can be administered to patients in the form of a single composition (e.g., multiple IR1-promoting agents, multiple leukocyte attractants, multiple antigen releasing agents, multiple type 1 lymphocyte attractants, multiple nutritional supplements, and chemically compatible combinations of these ingredients). By way of example, a composition that is useful in the therapeutic methods described herein comprises both a leukocyte attractant and at least one IR1-promoting agent.

Kits

The invention also includes kits that include one or more of the compositions described herein. Various kits combine, in a single package or in a plurality of packages that are sold, shipped, or promoted for complementary use, one or more of the compositions (e.g., in bulk packages or unit dosage forms), equipment or devices (e.g., electrodes or syringes), and instructional materials described herein. The instructional material can be a printed material, an audio or visual material, a computer-readable document or presentation, or any other tangible medium of expression whereby use of one or more of the methods and compositions described herein is explained to a medical practitioner, to a patient, or both. The instructional material need not be a single instructional material, but can be a series of pamphlets, videotapes, audio recordings, product package inserts, and the like. These materials can be provided together or separately with various compositions and devices described herein, or they can be provided separately with the intention that the materials will be used in conjunction with compositions or devices described herein in order to perform one of the therapeutic methods described herein.

Medical information obtained from patients undergoing a therapy described herein can be assembled in various ways to make a database. In this database, treatment parameters (e.g., type and dose of various agents, dosing schedule, and the like) can be correlated with the characteristics of the patient (e.g., age, gender, general state of health), the disease being treated (e.g., with the tumor type or stage of progression), with the outcome that is achieved (e.g., the rapidity with which the tumor is shrunk), and with any information relating to recurrence. The resulting database can be consulted when therapy of a new patient is undertaken, so that the method used to treat that patient can be matched with therapies which resulted in a favorable outcome in similar patients. This database can be provided (e.g., in the form of a computer-readable database) to users of the compositions, kits, and methods described herein, or it can be consulted by experts who communicate with those users.

EXAMPLES

The invention is now described with reference to the following Examples. These Examples are provided for the purpose of illustration only and the invention is not limited to these Examples, but rather encompass all variations which are evident as a result of the teaching provided herein.

Example 1

A patient diagnosed with a breast tumor mass having a diameter of 5 centimeters is treated using the anti-tumor treatment described herein, as follows.

A 500 milliliter sample of the patient's peripheral blood is withdrawn, and the cells are expanded in vitro, using a method described in the Detailed Description or in the prior art. The patient is instructed to begin taking a multi-vitamin formula including daily amounts of 300 milligrams of vitamin C, 300 IU of vitamin E, 200 micrograms of selenium, and 50 milligrams of zinc. The total dosage of the supplement is divided in three equal doses, one to be taken with each of the three daily meals.

After five days, the patient is prepared for tumor de-bulking by being immobilized in a bed and given a local anesthetic to desensitize the nerves of the breast tissue. With the assistance of live digital imaging, one electrode (negative polarity) is inserted in the center of the tumor mass, and two electrodes (each positive polarity) are inserted, one in each end of the tumor, about 2 centimeters from the center. Electric current is activated, and performed as described in the Detailed Description, for a duration of 2 hours. Thereafter, the patient rests for six hours.

In order to promote tumor leukocyte infiltration, a suspension comprising human IFN-g, TFN-a, IP-10, and Mig, each at a concentration specified in the Detailed Description. The suspension is injected at five points distributed equally at the tumor periphery, each injection containing about twenty microliters of the suspension. The patient remains at rest for 24 hours.

The patient is injected with an inflammation polarizing mixture comprising IFN-g, TNF-b, and IL-2, each at a concentration specified in the Detailed Description. This polarizing mixture is injected twice more, at 48 and 96 hours after the initial injection.

One hour later, about five billion expanded peripheral blood lymphocytes (expanded from the patient's blood sample) are injected peri-tumorally, at five different sites surrounding the tumor. An injection of the expanded cells is made into each of the three holes created by the electrical de-bulking treatment, and two more injections are made in the periphery of the tumor. An aliquot of the suspension comprising IFN-g, IL-2, and TNF-a is injected intra-tumorally (although this suspension can, alternatively, be combined with the cell suspension prior to peri-tumoral infusion of the cells). This amplification step is repeated every two or three days until the tumor has regressed to about 10 percent of its original size.

IL-15 is injected at the tumor site, as described in the Detailed Description, in order to terminate the type 1 inflammation by converting activated T cells into memory cells. The patient is thereafter discharged, and monthly follow-up sessions are scheduled.

Example 2

A patient in a poor nutritional state caused by a wide, thin stomach tumor covering the right wall of his stomach is treated using the anti-tumor treatment described herein.

The patient is placed on intravenous nutrition, including the daily nutritional requirements described in the Detailed Description. This treatment is continued for six days in order to partially replenish the patient's nutritional state.

Hexadecylphosphocholine (in an amount described in the Detailed Description) is injected at a plurality of points within the tumor, the injections being guided by live digital imaging. A mixture of proteases, as described in the Detailed Description, is injected at a plurality of points in the tumor. The inflammation at the tumor site is monitored after 24 hours, and the tumor should exhibit much infiltration and inflammation, as is characteristic of stomach tumors.

A suspension comprising IFN-g, TNF-b, and IL-2, in amounts specified in the Detailed Description, is injected at several points in the tumor mass in order to polarize the inflammatory response to a type 1 response in the tumor tissue. The tumor is monitored daily, and the polarizing suspension is injected into the tumor every 48 hours. After five days on this regimen, the tumor is anticipated to regress at a rate of about 10 percent of its total surface per day. After 8 more days, the tumor is anticipated to have shrunk to about 15 percent of its original size, but the tissues surrounding the tumor are anticipated to have become inflamed, and the patient experiences stomach pain.

The polarization treatment is discontinued, and IFN-a is injected into the tumor mass in order to halt the inflammatory response and induce memory cell production. IFN-a is also injected into the inflamed tissue surrounding the remaining tumor every two or three days, until the tumor has substantially disappeared, and the inflammation has diminished considerably.

Oral nutritional intake can then be re-established in the patient. Once this is re-established, the patient is discharged and monthly follow-up monitoring sessions are scheduled.

The disclosure of every patent, patent application, and publication cited herein is hereby incorporated herein by reference in its entirety.

While this invention has been disclosed with reference to specific embodiments, it is apparent that other embodiments and variations of this invention can be devised by others skilled in the art without departing from the true spirit and scope of the invention. The appended claims include all such embodiments and equivalent variations.

I claim:

1. A method of inducing tumor cell death in a human patient by inducing a type 1 inflammatory response in a solid tumor, the method comprising
   i) locally administering an antigen-releasing agent to a solid tumor in the patient, whereby a tumor antigen is released from cells of the tumor;
   iia) locally administering to the tumor a leukocyte attractant, whereby leukocytes are induced to infiltrate the tumor; and
   iib) locally administering to the tumor interferon-gamma (IFN-g) as a first tyne 1 inflammatory response promoting agent and a second type 1 inflammatory response-(IR1-)promoting agent selected from the group consisting of tumor necrosis factor-beta (TNF-b), tumor necrosis factor-alpha (TNF-a), interleukin-2 (IL-2), interleukin-12 (IL-12), and a mixture thereof whereby a type 1 inflammatory response is induced in the tumor and tumor cell death is induced.

2. The method of claim 1, wherein the antigen-releasing agent is a tumor de-bulking agent.

3. The method of claim 1, wherein the antigen-releasing agent comprises an agent selected from the group consisting of a proteolytic enzyme, an apoptosis-inducing agent, electrical current, an acid selected from the group consisting of hydrochloric acid and sulfuric acid, a base selected from the group consisting of sodium hydroxide and potassium hydroxide; and a mixture thereof.

4. The method of claim 3, wherein the antigen-releasing agent comprises a proteolytic enzyme selected from the group consisting of trypsin, chymotrypsin, pepsin, collagenase, and a mixture thereof.

5. The method of claim 3, wherein the antigen-releasing agent comprises only one proteolytic enzyme.

6. The method of claim 3, wherein the antigen-releasing agent comprises at least two proteolytic enzymes.

7. The method of claim 3, wherein the antigen-releasing agent comprises an alkylphospholipid.

8. The method of claim 7, wherein the alkylphospholipid is an alkylphosphocholine.

9. The method of claim 7, wherein the alkylphosphocholine is selected from the group consisting of hexadecylphosphocholine, edelfosine, and a mixture thereof.

10. The method of claim 3, wherein the antigen-releasing agent is electrical current delivered by way of electrodes inserted into the tumor.

11. The method of claim 3, wherein the antigen-releasing agent comprises an acid selected from the group consisting of hydrochloric acid, sulfuric acid, and a mixture thereof.

12. The method of claim 3, wherein the antigen-releasing agent comprises a base selected from the group consisting of sodium hydroxide, potassium hydroxide, and a mixture thereof.

13. The method of claim 1, wherein the antigen-releasing agent is administered to the tumor at least two hours before administering the leukocyte attractant to the tumor.

14. The method of claim 1, wherein the antigen-releasing agent and the leukocyte attractant are co-administered to the tumor.

15. The method of claim 1, wherein the antigen-releasing agent is administered to the tumor at least two hours before administering IFN-g to the tumor.

16. The method of claim 1, wherein the antigen-releasing agent and the IFN-g are co-administered to the tumor.

17. The method of claim 1, wherein the leukocyte attractant comprises a monocyte attractant.

18. The method of claim 17, wherein the monocyte attractant is selected from the group consisting of MCP-1, MCP-2, MCP-3, and MCP-4, and a mixture thereof.

19. The method of claim 1, wherein the leukocyte attractant comprises a T cell attractant.

20. The method of claim 19, wherein the T cell attractant is selected from the group consisting of RANTES, IP-10, and Mig, and a mixture thereof.

21. The method of claim 1, wherein the leukocyte attractant comprises a granulocyte attractant.

22. The method of claim 21, wherein the granulocyte attractant is selected from the group consisting of interleukin-8, granulocyte chemotactic protein-2, growth-related oncogen-1, growth-related oncogen-2, growth-related oncogen-3, neutrophil activated protein, neurotactin, and a mixture thereof.

23. The method of claim 21, wherein the granulocyte attractant is a eosinophil attractant.

24. The method of claim 23, wherein the eosinophil attractant is eotaxin.

25. The method of claim 1, wherein the leukocyte attractant is co-administered with at least one of IFN-g and the second IR1-promoting agent.

26. The method of claim 1, wherein the leukocyte attractant and at least one of IFN-g and the second IR1-promoting agent are administered not more than two hours apart.

27. The method of claim 1, wherein the leukocyte attractant and at least one of IFN-g and the second IR1-promoting agent are administered more than two hours apart.

28. The method of claim 1, wherein the leukocyte attractant and at least one of IFN-g and the second IR1-promoting agent are co-administered.

29. The method of claim 1, which further comprises administering at least one additional IR1-promoting agent is selected from the group consisting of interleukin-2 (IL-2), interleukin-12 (IL-12), tumor necrosis factor-alpha (TNF-a), and tumor necrosis factor-beta (TNF-b) and a mixture thereof.

30. The method of claim 29, wherein multiple aliquots of each of IFN-g, the second and the additional IR1-promoting agents are administered to the patient, and wherein at least 48 hours elapse between aliquots.

31. The method of claim 29, wherein IFN-g, the second and the additional IR1-promoting agents are co-administered.

32. The method of claim 29, wherein IFN-g, the second and the additional IR1-promoting agents are separately administered not more than two hours apart.

33. The method of claim 29, wherein IFN-g, the second and the additional IR1-promoting agents are separately administered more than two hours apart.

34. The method of claim 1, further comprising
  iii) locally administering to the tumor a type 1 lymphocyte attractant in order to sustain the type 1 inflammatory response.

35. The method of claim 34, wherein the type 1 lymphocyte attractant is selected from the group consisting of RANTES, IP-10, Mig, and a mixture thereof.

36. The method of claim 34, wherein two type 1 lymphocyte attractants are locally administered and wherein the type 1 lymphocyte attractants are IP-10 and Mig.

37. The method of claim 34, further comprising
  iv) sustaining the type 1 inflammatory response by locally administering autologous leukocytes to the tumor.

38. The method of claim 34, further comprising
  iv) administering a memory cell-inducing agent to the patient after inducing the type 1 inflammatory response, whereby production of anti-tumor type 1 immune memory cells is enhanced.

39. The method of claim 38, further comprising
  v) supplementing the patient's nutrition with a nutrient selected from the group consisting of a vitamin, a mineral, and a mixture thereof.

40. The method of claim 34, further comprising
  iv) supplementing the patient's nutrition with a nutrient selected from the group consisting of a vitamin, a mineral, and a mixture thereof.

41. The method of claim 1, further comprising
  iii) locally administering autologous leukocytes to the tumor.

42. The method of claim 41, wherein the autologous leukocytes are obtained from the patient and expanded prior to locally administering them to the tumor.

43. The method of claim 41, wherein the autologous leukocytes are obtained from the patient and contacted with one or more IR1-promoting agent prior to locally administering them to the tumor.

44. The method of claim 41, wherein the autologous leukocytes are obtained from the patient, expanded ex vivo, and contacted with one or more IR1-promoting agent prior to locally administering them to the tumor.

45. The method of claim 44, wherein the leukocytes are contacted with both the one or more IR1-promoting agent and with at least one of interferon-alpha (IFN-a) and IL-12 prior to locally administering them to the tumor.

46. The method of claim 41, further comprising
  iv) administering a memory cell-inducing agent to the patient after inducing the type 1 inflammatory response, whereby production of anti-tumor type 1 immune memory cells is enhanced.

47. The method of claim 46, further comprising
  v) supplementing the patient's nutrition with a nutrient selected from the group consisting of a vitamin, a mineral, and a mixture thereof.

48. The method of claim 41, further comprising
  iv) supplementing the patient's nutrition with a nutrient selected from the group consisting of a vitamin, a mineral, and a mixture thereof.

49. The method of claim 1, further comprising
iii) administering a memory cell-inducing agent to the patient after inducing the type 1 inflammatory response, whereby production of anti-tumor type 1 immune memory cells is enhanced.

50. The method of claim 49, wherein the memory cell-inducing agent is selected from the group consisting of interleukin-15 (IL-15), IFN-a, and a mixture thereof.

51. The method of claim 49, wherein the memory cell-inducing agent is IL-15.

52. The method of claim 49, wherein the memory cell-inducing agent is IFN-a.

53. The method of claim 49, wherein the memory cell-inducing agent is administered after the tumor shrinks to less than 10 percent of its size, immediately prior to administration of the memory cell inducing agent.

54. The method of claim 1, further comprising supplementing the patient's nutrition with a nutrient selected from the group consisting of a vitamin, a mineral, and a mixture thereof.

55. The method of claim 54, wherein the vitamin is selected from the group consisting of vitamins A, B, C, D, E, and a mixture thereof.

56. The method of claim 55, wherein the vitamin is vitamin C and wherein the patient's nutrition is supplemented such that the patient receives from 200 to 400 milligrams of vitamin C daily.

57. The method of claim 55, wherein the vitamin is vitamin E and wherein the patient's nutrition is supplemented such that the patient receives from 200 to 400 international units of vitamin E daily.

58. The method of claim 54, wherein the mineral is selected from the group consisting of selenium, zinc, calcium, magnesium, iron, copper, and a mixture thereof.

59. The method of claim 58, wherein the mineral is selenium and wherein the patient's nutrition is supplemented such that the patient receives from 200 to 400 micrograms of selenium daily.

60. The method of claim 58, wherein the mineral is zinc and wherein the patient's nutrition is supplemented such that the patient receives from 15 to 100 milligrams of zinc daily.

61. The method of claim 54, wherein the patient's nutrition is supplemented beginning at least on the same day that the antigen-releasing agent is administered to the tumor, and continuing through at least the same day that IFN-g is administered to the tumor.

62. The method of claim 54, wherein the patient's nutrition is supplemented beginning at least five days before the antigen-releasing agent is administered to the tumor, and continuing through at least three days after the day that IFN-g is administered to the tumor.

63. A method of inducing tumor cell death in a human patient by inducina a type 1 inflammatory response in a solid tumor, the method comprising
i) supplementing the patient's nutrition with a nutrient selected from the group consisting of a vitamin, a mineral, and a mixture thereof;
ii) locally administering an antigen-releasing agent to a solid tumor in the patient, whereby a tumor antigen is released from cells of the tumor; thereafter
iiia) locally administering to the tumor a leukocyte attractant, whereby leukocytes are induced to infiltrate the tumor; and
iiib) locally administering to the tumor interferon-gamma (IFN-g) as a first type 1 inflammatory response promoting agent and a second type 1 inflammatory response-(IR1-)promoting agent, selected from the group consisting of tumor necrosis factor-beta (TNF-b), tumor necrosis factor-alpha (TNF-a), interleukin-2 (IL-2), interleukin-12 (IL-12), and a mixture thereof whereby a type 1 inflammatory response is induced in the tumor; thereafter
iv) sustaining the type 1 inflammatory response by
iva) locally administering to the tumor a type 1 lymphocyte attractant,
ivb) locally administering autologous leukocytes to the tumor, or
ivc) both iva) and ivb); and thereafter
v) administering a memory cell-inducing agent to the patient after inducing the type 1 inflammatory response, whereby production of anti-tumor type 1 immune memory cells is enhanced and tumor cell death is induced.

64. A method of inducing a type 1 inflammatory response at the site of a solid tumor in a human patient, the method comprising locally co-administering to the tumor p1 i) an antigen-releasing agent;
ii) a leukocyte attractant; and
iii) interferon-gamma (IFN-g) as a first type 1 inflammatory response promoting agent and a second type 1 inflammatory response-(IR1-) promoting agent selected from the group consisting of tumor necrosis factor beta (TNF-b), tumor necrosis factor-alpha (TNF-a), interleukin-2 (Il -2), interleukin-12 (Il -12), and a mixture thereof.

* * * * *